US012761178B2

(12) United States Patent
Bedau

(10) Patent No.: US 12,761,178 B2
(45) **Date of Patent: *Oct. 13, 2026**

(54) LOW NOISE AMPLIFIERS WITH SHIELDS FOR NANOPORE APPLICATIONS

(71) Applicant: Western Digital Technologies, Inc., San Jose, CA (US)

(72) Inventor: Daniel Bedau, San Jose, CA (US)

(73) Assignee: Western Digital Technologies, Inc., San Jose, CA (US)

( * ) Notice: Subject to any disclaimer, the term of this patent is extended or adjusted under 35 U.S.C. 154(b) by 278 days.

This patent is subject to a terminal disclaimer.

(21) Appl. No.: 18/406,202

(22) Filed: Jan. 7, 2024

(65) Prior Publication Data

US 2024/0142399 A1 May 2, 2024

Related U.S. Application Data

(63) Continuation of application No. 17/651,257, filed on Feb. 16, 2022, now Pat. No. 11,940,404.

(51) Int. Cl.

| | |
|---|---|
| ***G01N 27/22*** | (2006.01) |
| ***G01N 33/487*** | (2006.01) |
| ***H03F 3/04*** | (2006.01) |

(52) U.S. Cl.

CPC ......... *G01N 27/226* (2013.01); *G01N 27/228* (2013.01); *G01N 33/48721* (2013.01); *H03F 3/04* (2013.01); *H03F 2200/294* (2013.01)

(58) Field of Classification Search

CPC ............... G01N 27/226; G01N 27/228; G01N 33/48721; H03F 3/04

See application file for complete search history.

(56) References Cited

U.S. PATENT DOCUMENTS

| | | | |
|---|---|---|---|
| 7,075,161 | B2 | 7/2006 | Barth |
| 8,669,124 | B2 | 3/2014 | Merz |

(Continued)

FOREIGN PATENT DOCUMENTS

| | | | |
|---|---|---|---|
| CA | 2869753 | A1 | 10/2013 |
| CN | 209342031 | | 9/2019 |

(Continued)

OTHER PUBLICATIONS

B. Goldstein, D. Kim, M. Magoch, Y. Astier and E. Culurciello, "CMOS low current measurement system for nanopore sensing applications," 2011 IEEE Biomedical Circuits and Systems Conference (BioCAS), 2011, pp. 265-268, doi: 10.1109/BioCAS.2011.6107778.

(Continued)

*Primary Examiner* — Alvaro E Fortich

(57) ABSTRACT

Disclosed herein are systems for detecting molecules. In some embodiments, a system includes a multiplexer, a read amplifier coupled to the multiplexer, a digitizer coupled to the read amplifier, a first nanopore, a first sense electrode situated on a first side of the first nanopore, a first counter electrode situated on a second side of the first nanopore, a first shield at least partially surrounding the first sense electrode and coupled to the multiplexer, a first shield driver coupled to the first shield, drive circuitry coupled to the first sense electrode, and control logic coupled to the drive circuitry, the multiplexer, and to the digitizer. In some embodiments, the control logic is configured to control the drive circuitry and/or the multiplexer to select the first sense electrode and/or the first counter electrode, and obtain a digitized signal from the digitizer, the digitized signal representing a current through the first nanopore.

19 Claims, 11 Drawing Sheets

(56) References Cited

U.S. PATENT DOCUMENTS

| | | | |
|---|---|---|---|
| 8,860,438 B2 | 10/2014 | Zhang | |
| 9,217,727 B2 | 12/2015 | Rosenstein et al. | |
| 9,322,820 B2 | 4/2016 | Blick et al. | |
| 9,650,670 B2 | 5/2017 | Kim et al. | |
| 9,869,702 B2 | 1/2018 | Kuramochi | |
| 11,181,504 B2 | 11/2021 | Washizu | |
| 11,571,148 B1 | 2/2023 | Puttananjegowda et al. | |
| 11,624,727 B2 | 4/2023 | Rosenstein et al. | |
| 11,833,346 B2 | 12/2023 | Park et al. | |
| 2008/0248561 A1 | 10/2008 | Golovchenko et al. | |
| 2011/0133255 A1 | 6/2011 | Merz | |
| 2013/0048499 A1 | 2/2013 | Mayer et al. | |
| 2013/0180867 A1 | 7/2013 | Rosenstein et al. | |
| 2014/0048416 A1 | 2/2014 | Rosenstein et al. | |
| 2014/0221249 A1 | 8/2014 | Chen et al. | |
| 2015/0060276 A1 | 3/2015 | Golovchenko et al. | |
| 2015/0060277 A1 | 3/2015 | Golovchenko et al. | |
| 2015/0337367 A1 | 11/2015 | Kim et al. | |
| 2015/0369776 A1 | 12/2015 | Rosenstein et al. | |
| 2015/0377856 A1 | 12/2015 | Dunbar et al. | |
| 2016/0154032 A1* | 6/2016 | Kuramochi | G01R 19/0023 324/120 |
| 2017/0145481 A1 | 5/2017 | Kim et al. | |
| 2018/0238824 A1 | 8/2018 | Lee et al. | |
| 2019/0004027 A1 | 1/2019 | Chen et al. | |
| 2019/0154623 A1 | 5/2019 | Chen | |
| 2020/0033292 A1 | 1/2020 | Washizu | |
| 2020/0292594 A1 | 9/2020 | Hsu et al. | |
| 2021/0148886 A1* | 5/2021 | Maney, Jr. | G01N 33/48721 |
| 2021/0300750 A1 | 9/2021 | Waterman | |
| 2023/0172495 A1 | 6/2023 | Puttananjegowda et al. | |

FOREIGN PATENT DOCUMENTS

| | | | |
|---|---|---|---|
| CN | 111090002 | A | 5/2020 |
| CN | 112292462 | A | 1/2021 |
| CN | 112924745 | A | 6/2021 |
| EP | 2734839 | A1 | 5/2014 |
| EP | 2815425 | A4 | 10/2015 |
| KR | 102059488 | B1 | 12/2019 |
| WO | 2010020912 | A1 | 2/2010 |
| WO | 2012116161 | A1 | 8/2012 |
| WO | 2014066909 | A1 | 5/2014 |
| WO | 2020183172 | A1 | 9/2020 |

OTHER PUBLICATIONS

Beamish, E., Kwok, H., Tabard-Cossa, V., Godin, M. "Fine-tuning the Size and Minimizing the Noise of Solid-state Nanopores." J. Vis. Exp. (80), e51081, doi:10.3791/51081 (2013).

C. Hoyle and A. Peyton, "Bootstrapping techniques to improve the bandwidth of transimpedance amplifiers," IEE Colloquium on Analog Signal Processing (Ref. No. 1998/472), 1998, pp. 7/1-7/6, doi: 10.1049/ic:19980849.

Camilla L.C. Ip et al., "MinION Analysis and Reference Consortium: Phase 1 data release and analysis," F1000Research 2015, 4:1075 Last updated: May 23, 2017.

Ciccarella, P., Carminati, M., Ferrari, G., Fraccari, R.L., & Bahrami, A. "Integrated low-noise current amplifier for glass-based nanopore sensing." 2014 10th Conference on Ph.D. Research in Microelectronics and Electronics (PRIME), 1-4 (2014).

D. V. Barkovaa et al., "Channel and Motor Proteins for Translocation of Nucleic Acids in Nanopore Sequencing," ISSN 0027-1314, Moscow University Chemistry Bulletin, 2020, vol. 75, No. 3, pp. 149-161.

International Search Report and Written Opinion from PCT Application No. PCT/US2022/030440 (filed May 22, 2022), mailed Nov. 3, 2022.

International Search Report and Written Opinion from PCT Application No. PCT/US2022/030441 (filed May 22, 2022), mailed Dec. 1, 2022.

J. Rosenstein, V. Ray, M. Drndic and K. L. Shepard, "Solid-state nanopores integrated with low-noise preamplifiers for high-bandwidth DNA analysis," 2011 IEEE/NIH Life Science Systems and Applications Workshop (LiSSA), 2011, pp. 59-62, doi: 10.1109/LISSA.2011.5754155.

P. Horowitz and W. Hill, "The Art of Electronics, 3rd Edition," Cambridge University Press, 2015.

Patrick S Spinney et al., "Fabrication and characterization of a solid-state nanopore with self-aligned carbon nanoelectrodes for molecular detection," Nanotechnology, vol. 23, No. 13, 2012.

Rosenstein, J., Wanunu, M., Merchant, C. et al. "Integrated nanopore sensing platform with sub-microsecond temporal resolution." Nat Methods 9, 487-492 (2012). https://doi.org/10.1038/nmeth.1932.

Shengfa Liang et al., "Noise in nanopore sensors: Sources, models, reduction, and benchmarking," Nanotechnology and Precision Engineering 3 (2020) 9-17.

Stephen Jordan Fleming, "Probing nanopore—DNA interactions with MspA," Nov. 2017.

V. Dimitrov et al., "Nanopores in solid-state membranes engineered for single molecule detection," Nanotechnology, vol. 21, No. 6, Jan. 11, 2010.

Yun et al. "An integrated potentiostat sensor with digitally-controlled input-parasitic compensation fornanopore applications." In: 2015 IEEE Sensors, IEEE, Nov. 4, 2015, pp. 1-4.

Zhen Gu, "Ultra-low noise measurements of nanopore-based single molecular detection," Sep. 2017, Science Bulletin 62(18).

Rosenstein, J.K., et al., "Temporal resolution of nanopore sensor recordings", 35th Annual International Conference of the IEEE, pp. 4110-4113, (Jul. 3-7, 2013).

Chi, Y.M., et al., "Ultra-High Input Impedance, Low Noise Integrated Amplifier for Noncontact Biopotential Sensing" IEEE Journal, vol. 1, Issue No. 4, pp. 526-535, (Dec. 2011).

* cited by examiner

LOW NOISE AMPLIFIERS WITH SHIELDS FOR NANOPORE APPLICATIONS

CROSS-REFERENCE TO RELATED APPLICATIONS

This application is a continuation of, and hereby incorporates by reference in its entirety for all purposes, U.S. patent application Ser. No. 17/651,257, filed Feb. 16, 2022 and entitled "LOW NOISE AMPLIFIERS WITH SHIELDS FOR NANOPORE APPLICATIONS." This application hereby incorporates by reference in its entirety for all purposes U.S. patent application Ser. No. 17/651,254, filed Feb. 16, 2022 and entitled "LOW NOISE AMPLIFIERS WITH FEEDBACK FOR NANOPORE APPLICATIONS."

BACKGROUND

Nanopores are small holes, typically 1-2 nanometers (nm) in diameter and a couple of nanometers thick, that can be used to observe single molecules at high throughput and with relatively fine temporal resolution. Nanopores can be used to read molecules (e.g., biomolecules) for applications such as DNA sequencing, DNA/RNA storage applications, and bioanalytical sensing.

There are two types of nanopore: biological nanopores (also referred to as protein nanopores) and solid-state nanopores. A biological nanopore is made from a pore material embedded in a lipid membrane. A solid-state nanopore is a nanoscale (e.g., nanometer-sized) opening in a synthetic membrane (e.g., SiNx, $SiO_2$, etc.).

A target molecule in an electrolyte solution can be driven through a nanopore (either biological or solid-state) by electrophoresis. A highly-focused external electric field applied transverse to and in the vicinity of the nanopore (e.g., by electrodes used to read or detect the molecule) acts on a relatively short segment of the negatively charged molecule and directs it through the hole in the nanopore.

An ionic current can be generated across the nanopore by applying a bias voltage. As a molecule passes through a nanopore, the ions occupying the pore are displaced, which causes changes in the ionic current measured across the nanopore. These changes in the ionic current can be observed and used to detect constituent parts of the molecule (e.g., nucleotides of a DNA strand). For example, by analyzing the amplitudes, durations, frequencies, and/or shapes of the blockade events, various properties of the target molecule can be deduced.

As a specific example, as nucleic acid moves, or translocates, through a nanopore, different nucleotides cause different ionic current patterns. Specifically, the nucleotides cause distinct, measurable ionic current blockades, or current drops, as they pass through the nanopore. The current blockades can be recorded (e.g., using a current amplifier) and converted into digital signals (e.g., using an analog-to-digital converter). These current blockades, or patterns of them, can be used to distinguish between different nucleotides.

One challenge with using nanopores is that detection relies on the ability to detect small differences in the ionic current (e.g., on the order of picoamperes) as a molecule translocates through the nanopore. Noise in the ionic current measurement limits the signal-to-noise ratio (SNR) and the effective time resolution of the detection. The noise is dependent on any capacitance present at the input to the amplifier that senses and amplifies the ionic current signal. For solid-state nanopores, the total capacitance includes the capacitance of the thin membrane in which the nanopore is fabricated, the capacitance of the wiring between the electrodes and the amplifier, and the characteristic capacitance of the amplifier at its input. The capacitance at the input to the amplifier forms a pole with the output impedance of the amplifier. High capacitance at the input to the amplifier can cause noise peaking and SNR degradations.

Thus, there is a need to reduce noise in the detected ionic current.

SUMMARY

This summary represents non-limiting embodiments of the disclosure.

In some aspects, the techniques described herein relate to a device for detecting molecules, the device including: a multiplexer; a read amplifier coupled to the multiplexer; a digitizer coupled to the read amplifier; a first nanopore; a first sense electrode situated on a first side of the first nanopore; a first counter electrode situated on a second side of the first nanopore; a first shield, wherein the first shield at least partially surrounds the first sense electrode and is coupled to the multiplexer; a first shield driver coupled to the first shield; drive circuitry coupled to the first sense electrode; and control logic coupled to the drive circuitry, the multiplexer, and to the digitizer, wherein the control logic is configured to: control at least one of the drive circuitry or the multiplexer to select at least one of the first sense electrode or the first counter electrode, and obtain a digitized signal from the digitizer, the digitized signal representing a current through the first nanopore.

In some aspects, the device further includes an interface coupled to the control logic, and wherein the control logic is further configured to make the digitized signal available via the interface.

In some aspects, the first nanopore includes a first hole, and wherein the first shield is recessed from the first hole.

In some aspects, the drive circuitry includes a voltage source.

In some aspects, the digitized signal is a first digitized signal, and the device further includes: a second nanopore; a second sense electrode situated on a first side of the second nanopore; a second counter electrode situated on a second side of the second nanopore; a second shield, wherein the second shield at least partially surrounds the second sense electrode and is coupled to the multiplexer; and a second shield driver coupled to the second shield, and control logic is further configured to: control the at least one of the drive circuitry or the multiplexer to select at least one of the second sense electrode or the second counter electrode, and obtain a second digitized signal from the digitizer, the second digitized signal representing a current through the second nanopore.

In some aspects, the multiplexer is a first multiplexer, the read amplifier is a first read amplifier, and the digitizer is a first digitizer, and further including: a second multiplexer; a third nanopore; a third sense electrode situated on a first side of the third nanopore; a third counter electrode situated on a second side of the third nanopore; a third shield, wherein the third shield at least partially surrounds the third sense electrode and is coupled to the second multiplexer; a third shield driver coupled to the third shield; a second read amplifier coupled to the second multiplexer; and a second digitizer coupled to the second read amplifier, and wherein: the drive circuitry is further coupled to the third sense electrode, the control logic is further coupled to the second multiplexer and to the second digitizer, and the control logic is further configured to: control at least one of the drive circuitry or the second multiplexer to select at least one of the third sense electrode or the third counter electrode, and obtain a second digitized signal from the second digitizer, the second digitized signal representing a current through the third nanopore.

In some aspects, the techniques described herein relate to a system for detecting molecules, the system including: an array including: a first read amplifier; a first nanopore; a first sense electrode situated on a first side of the first nanopore; a first counter electrode situated on a second side of the first nanopore; a first shield, wherein the first shield at least partially surrounds the first sense electrode and is coupled to an output of the first read amplifier; a first shield driver coupled to the first shield; a second read amplifier; a second nanopore; a second sense electrode situated on a first side of the second nanopore; a second counter electrode situated on a second side of the second nanopore; and a second shield, wherein the second shield at least partially surrounds the second sense electrode and is coupled to an output of the second read amplifier; and a second shield driver coupled to the second shield; drive circuitry coupled to the array; a multiplexer, wherein a first input of the multiplexer is coupled to the first read amplifier and a second input of the multiplexer is coupled to the second read amplifier, and an output of the multiplexer is coupled to a digitizer; and control logic coupled to the drive circuitry, to the digitizer, and to the multiplexer, wherein the control logic is configured to: control at least one of the drive circuitry or the multiplexer to select at least one of the first sense electrode or the first counter electrode, and obtain a digitized signal from the digitizer, the digitized signal representing a current through the first nanopore.

In some aspects, the system further includes an interface coupled to the control logic, and the control logic is further configured to make the digitized signal available via the interface.

In some aspects, the first read amplifier includes a first transistor, and wherein the first shield is coupled to a source of the first transistor, and the first sense electrode is coupled to a gate of the first transistor; and the second read amplifier includes a second transistor, and wherein the second shield is coupled to a source of the second transistor, and the second sense electrode is coupled to a gate of the second transistor.

In some aspects, at least one of the first transistor or the second transistor is a field effect transistor or a bipolar junction transistor.

In some aspects, the first nanopore includes a first hole, and the first shield is recessed from the first hole, and the second nanopore includes a second hole, and the second shield is recessed from the second hole.

In some aspects, the digitized signal is a first digitized signal, and control logic is further configured to: control the at least one of the drive circuitry or the multiplexer to select at least one of the second sense electrode or the second counter electrode, and obtain a second digitized signal from the digitizer, the second digitized signal representing a current through the second nanopore.

In some aspects, the drive circuitry includes a voltage source.

In some aspects, the techniques described herein relate to a system for detecting molecules, the system including: an amplifier; a nanopore; a sense electrode situated on a first side of the nanopore; a counter electrode situated on a second side of the nanopore; and a shield, wherein: the sense electrode and the counter electrode are configured to sense a current through the nanopore, and the shield at least partially surrounds the sense electrode and is coupled to an output of the amplifier.

In some aspects, the system further includes a digitizer coupled to the output of the amplifier.

In some aspects, the system further includes a processor coupled to an output of the digitizer.

In some aspects, the nanopore includes a hole, and the shield is recessed from the hole.

In some aspects, the amplifier includes a transistor, and wherein the shield is coupled to a source of the transistor, and the sense electrode is coupled to a gate of the transistor. In some aspects, the transistor and the nanopore are integrated onto a same substrate. In some aspects, the nanopore includes a hole, and wherein the shield is recessed from the hole.

BRIEF DESCRIPTION OF THE DRAWINGS

Objects, features, and advantages of the disclosure will be readily apparent from the following description of certain embodiments taken in conjunction with the accompanying drawings in which.

Figure 1:
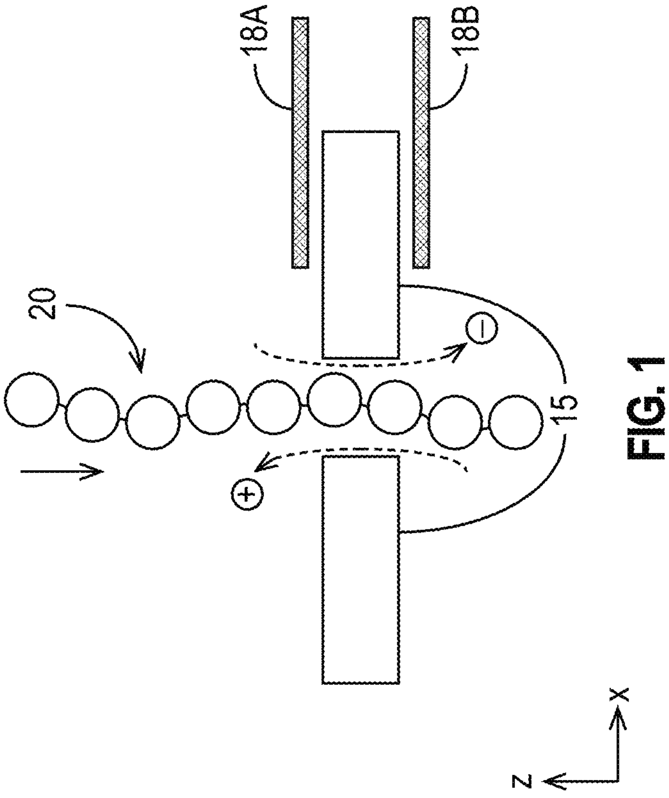
FIG. 1 illustrates a nanopore with a molecule passing through it in accordance with some embodiments.

To facilitate understanding, identical reference numerals have been used, where possible, to designate identical elements that are common to the figures. It is contemplated that elements disclosed in one embodiment may be beneficially utilized in other embodiments without specific recitation. Moreover, the description of an element in the context of one drawing is applicable to other drawings illustrating that element.

DETAILED DESCRIPTION

Disclosed herein are low-noise readout circuits, devices, and systems, and methods of using them. The disclosed circuits can substantially reduce amplifier input current noise in nanopore applications. A nanopore unit includes a shield situated between the sense electrode and the counter electrode. The shield can be coupled to an output of the amplifier so that the voltage on the shield substantially tracks the voltage of the sense electrode. The shield may be recessed from a hole in the nanopore. A system or device may include an array of nanopore units that may share some components, such as one or more of: a read amplifier, a digitizer, drive circuitry, control logic, and/or a multiplexer.

FIG. 1 illustrates a nanopore 15 with a molecule 20 (e.g., a single-stranded DNA (ssDNA) molecule), passing through it. Two electrodes, which are referred to herein as the sense electrode 18A and the counter electrode 18B, are situated near the nanopore 15 to sense the ionic or tunnel current through the nanopore 15. The sense electrode 18A and/or counter electrode 18B are typically connected to a voltage source (not illustrated), which creates a potential between the sense electrode 18A and counter electrode 18B.

Figure 2:
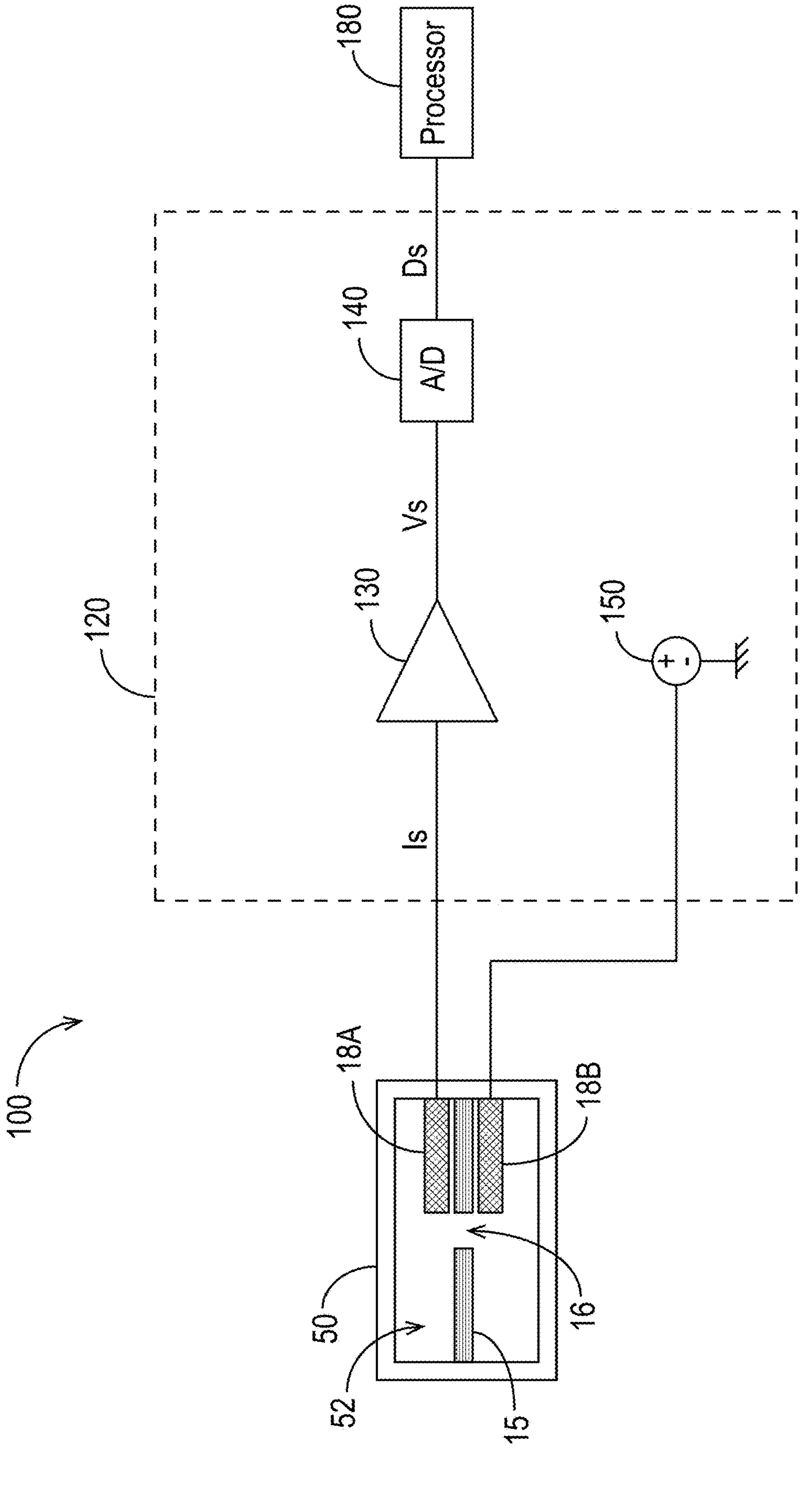
FIG. 2 is a diagram of a system for detecting molecules in accordance with some embodiments.

FIG. 2 is a diagram of a system 100 for detecting molecules in accordance with some embodiments. The system 100 includes a nanopore unit 50, a detection device 120, and a processing device 180. The illustrated nanopore unit 50 has a fluid chamber 52 that can be filled with an electrolyte solution containing molecules to be detected (e.g., molecule 20 from FIG. 1). The nanopore unit 50 includes a nanopore 15 with a hole 16. The sense electrode 18A and counter electrode 18B are situated on either side of the nanopore 15, as illustrated. As explained further below, the sense electrode 18A and/or counter electrode 18B may be in contact with the nanopore 15 or they may be separated from it.

In the diagram of FIG. 2, the detection device 120 comprises an amplifier 130, an analog-to-digital converter 140 (or, more generally, a digitizer), and a voltage source 150. The amplifier 130 may be, for example, a transimpedance amplifier that is configured to convert the detected current, Is, to a voltage, Vs. The analog-to-digital converter 140 is configured to digitize the output voltage, Vs, of the amplifier 130 and provide it to the processing device 180 (e.g., via an interface). The voltage source 150 is configured to generate a voltage of sufficient magnitude across the sense electrode 18A and counter electrode 18B to drive molecules within the fluid chamber 52 into the hole 16 and to allow the effect of the molecules on the current to be detected by the amplifier 130. The voltage source 150 may be capable of providing a variable voltage level Vb across the sense electrode 18A and counter electrode 18B. The amplifier 130 may operate by, for example, detecting the resistance between the sense electrode 18A and the counter electrode 18B when the voltage is applied by the voltage source 150.

In operation, the voltage source 150 generates a voltage across the sense electrode 18A and counter electrode 18B, which causes an ionic or tunnel current, Is, to flow between the sense electrode 18A and counter electrode 18B and also causes molecules in the fluid chamber 52 to be drawn into the hole 16 of the nanopore 15. If the voltage across the sense electrode 18A and counter electrode 18B is Vb, the current Is is given by Ohm's law: Is=Vb/Rp, where Rp is the resistance through the nanopore 15 encountered by a molecule 20 as it passes through the hole 16. The amplifier 130 converts the current Is to a voltage, Vs, which it passes to the analog-to-digital converter 140. The voltage Vs is dependent on the gain of the amplifier 130. The analog-to-digital converter 140 converts the voltage signal Vs into digital data Ds, which it passes to the processing device 180, which may be situated in a different (external) physical device than the nanopore unit 50 and/or detection device 120 (e.g., the nanopore unit 50 and/or detection device 120 may be situated on/in a single integrated circuit device, and the processing device 180 may be in a computer or other device external to the integrated circuit device). The analog-to-digital converter 140 may provide the sampled signal Ds to the processing device 180 using any available communication path (e.g., wired or wireless) and in accordance with any suitable protocol (e.g., IEEE 802.11, Ethernet, USB, etc.).

As described further below, multiple instantiations of the nanopore unit 50, the detection device 120, and/or the processing device 180 may be included in a single physical device, or they may be separate. For example, the nanopore unit 50 and the detection device 120 may be included in a single device that is connected to the processing device 180 (e.g., a computer or other processor). In addition, a system may include multiple nanopores 15 connected to sense electrodes 18A and counter electrodes 18B (which may be dedicated or shared), in turn coupled to detection devices 120 (which may be dedicated or shared) that measure the respective currents (Is).

Figure 3A:
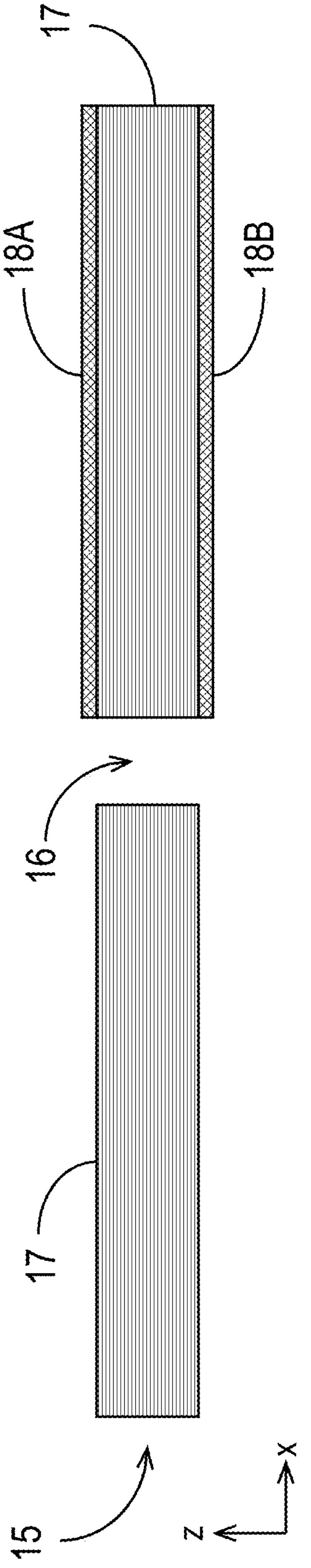
FIG. 3A illustrates a cross-section of an example configuration of a nanopore, a sense electrode, and a counter electrode in accordance with some embodiments.

FIG. 3A illustrates a cross-section of an example configuration of a nanopore 15 and the sense electrode 18A and counter electrode 18B in accordance with some embodiments. The cross-section is in the x-z plane, as indicated by the axes. As illustrated in the example of FIG. 3A, the nanopore 15 can comprise a thin dielectric layer 17 with a hole 16 and two electrodes, namely, the sense electrode 18A and counter electrode 18B, attached to the sides of the nanopore 15. The sense electrode 18A and counter electrode 18B may have thicknesses in the z-direction of, for example, around 10 nm.

Figure 3B:
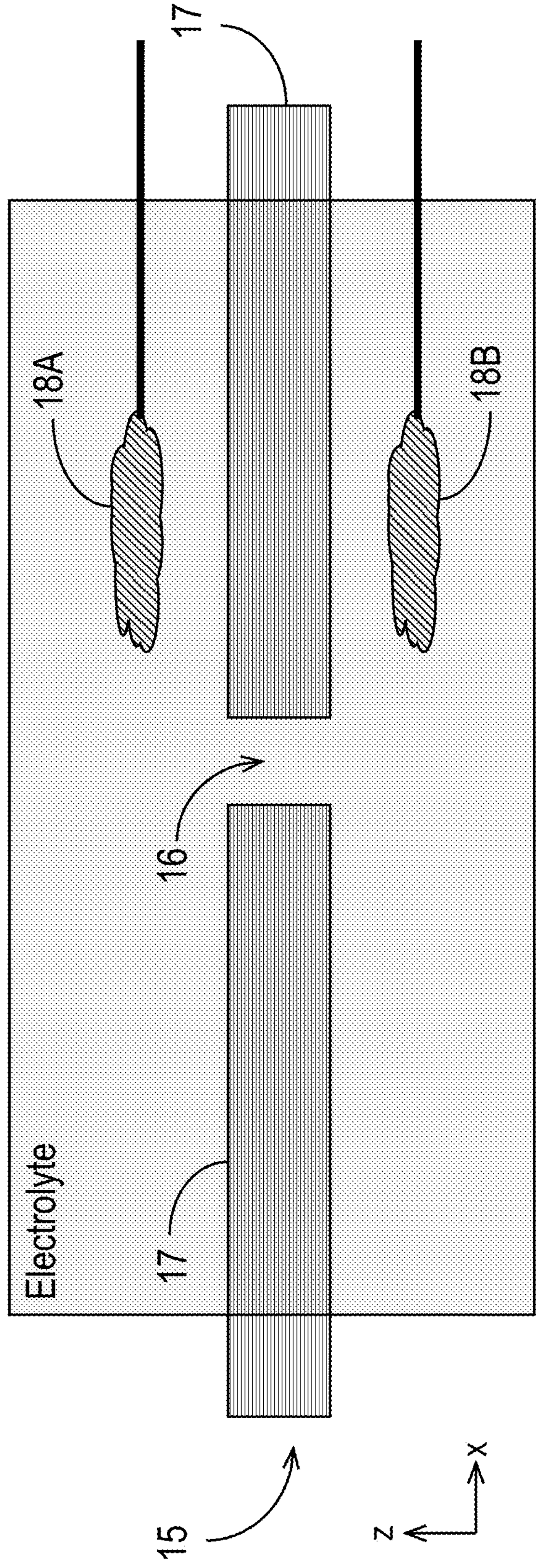
FIG. 3B illustrates a cross-section of an alternative example configuration of a nanopore, a sense electrode, and a counter electrode in accordance with some embodiments.

FIG. 3B illustrates a cross-section of an alternative example configuration of a nanopore 15 and the sense electrode 18A and counter electrode 18B in accordance with some embodiments. As illustrated in FIG. 3B, the sense electrode 18A and counter electrode 18B can be electrochemical electrodes, e.g. silver/silver-chloride pairs.

With either of the sense electrode 18A and counter electrode 18B embodiments illustrated in FIGS. 3A and 3B, the thin dielectric layer 17 of the nanopore 15 is very thin (e.g., in the nm range) to create a nanopore 15 with a suitable aspect ratio so that molecules passing through the hole 16 will cause measurable disturbances in the ionic or tunnel current. As a result, the capacitance between the sense electrode 18A and counter electrode 18B, which is inversely proportional to the thickness of the thin dielectric layer 17, is naturally very large. This capacitance can amplify the noise of the applied voltage Vb by forming a pole with the output impedance of the amplifier 130. It can also cause the detection device 120 to have an unstable dynamic response at higher frequencies. This instability can reduce the usefulness of the system 100 by preventing it from being able to detect rapid changes in the current as molecules pass through the nanopore 15 at the applied voltage Vb. Specifically, the capacitance amplifies the noise voltage, particularly at higher frequencies. The amplified noise limits the frequency at which the nanopore 15 can read or detect molecules passing through its hole 16.

Figure 4:
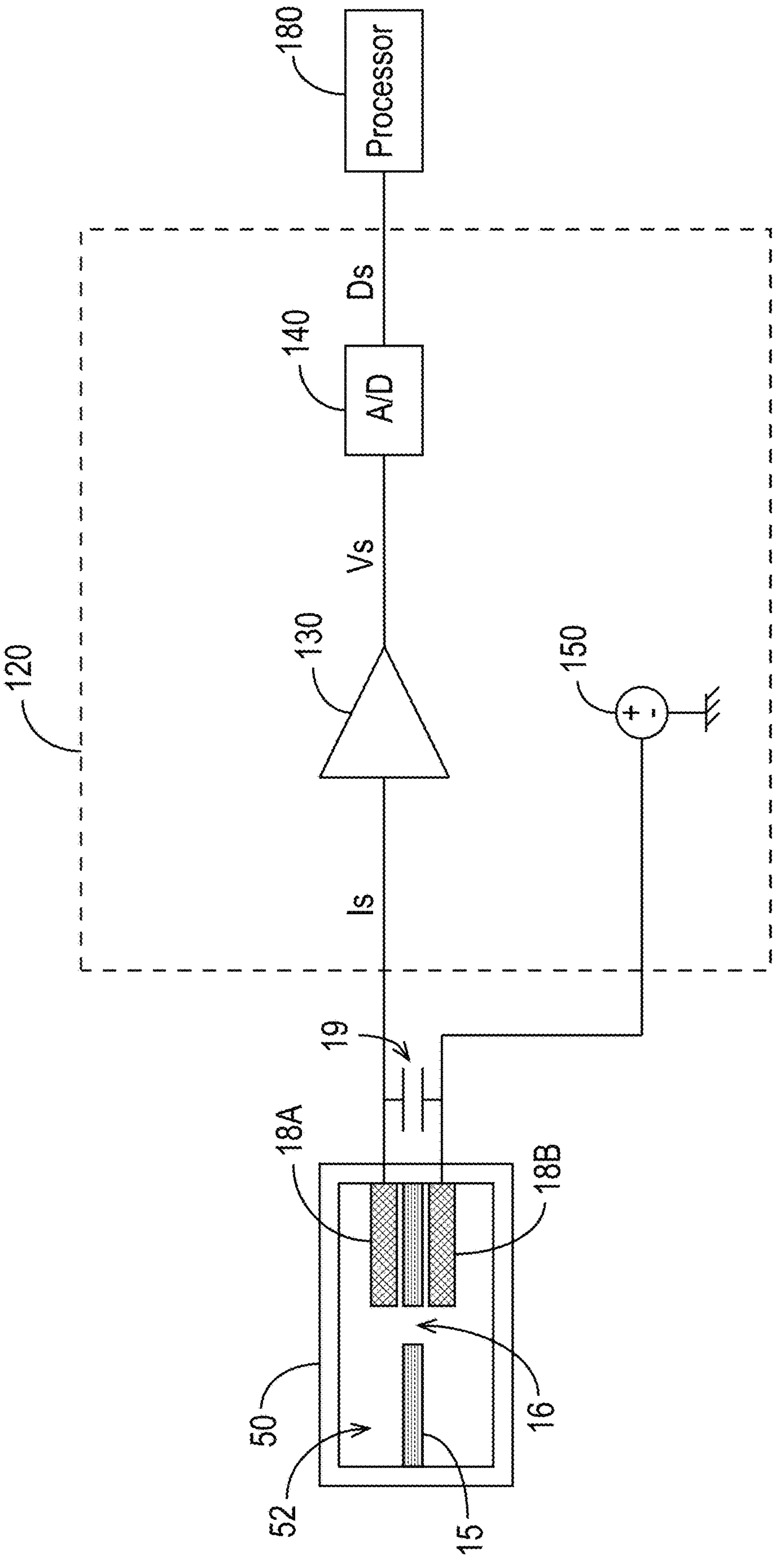
FIG. 4 is a conceptual illustration of the system of FIG. 2 with the parasitic capacitance between the sense electrode and the counter electrode represented as a capacitor in accordance with some embodiments.

The capacitance of the nanopore 15 can be modeled as the parallel-plate capacitance of the constituent elements of the nanopore unit 50. FIG. 4 is a conceptual illustration of the system 100 of FIG. 2 representing the capacitance between the sense electrode 18A and the counter electrode 18B as a capacitor. As illustrated in FIG. 4, the capacitance can be considered as a parasitic capacitance 19 between the sense electrode 18A and counter electrode 18B. The parasitic capacitance 19 acts as a charge sink for the sense electrode 18A and can create a peak in the noise spectrum. For example, if a potential difference ΔU is created between the sense electrode 18A and counter electrode 18B, a charge $Q=\Delta U*C$ flows into the parasitic capacitance 19, which reduces the signal (e.g., the current Is) that is sensed by the amplifier 130 and, correspondingly, reduces the SNR of the measurement.

Prior approaches to improving the SNR have included reducing the capacitance of the nanopore 15 by modifying its physical layout, reducing the bandwidth of the amplifier 130, and reducing the translocation speed of the molecules passing through the nanopore 15. All of these approaches have drawbacks. For example, changes to the physical layout are limited by manufacturability, and reduced amplifier 130 bandwidth and/or translocation speed of molecules through the nanopore 15 reduces the rate at which molecules can be read. Therefore, there remains a need for additional solutions.

Disclosed herein are devices, systems, and methods that can improve the SNR of nanopore 15 measurements by mitigating the effect of the parasitic capacitance 19. In some embodiments, a shield connected to the output of the amplifier 130 substantially mirrors changes in the potential of the sense electrode 18A, thereby allowing the parasitic capacitance 19 to be partially or completely canceled. In some embodiments, the effects of the parasitic capacitance 19 between the sense electrode 18A and the counter electrode 18B are mitigated by a shield situated between the sense electrode 18A and the counter electrode 18B. The shield may be referred to as a shield electrode or simply a shield.

Figure 5A:
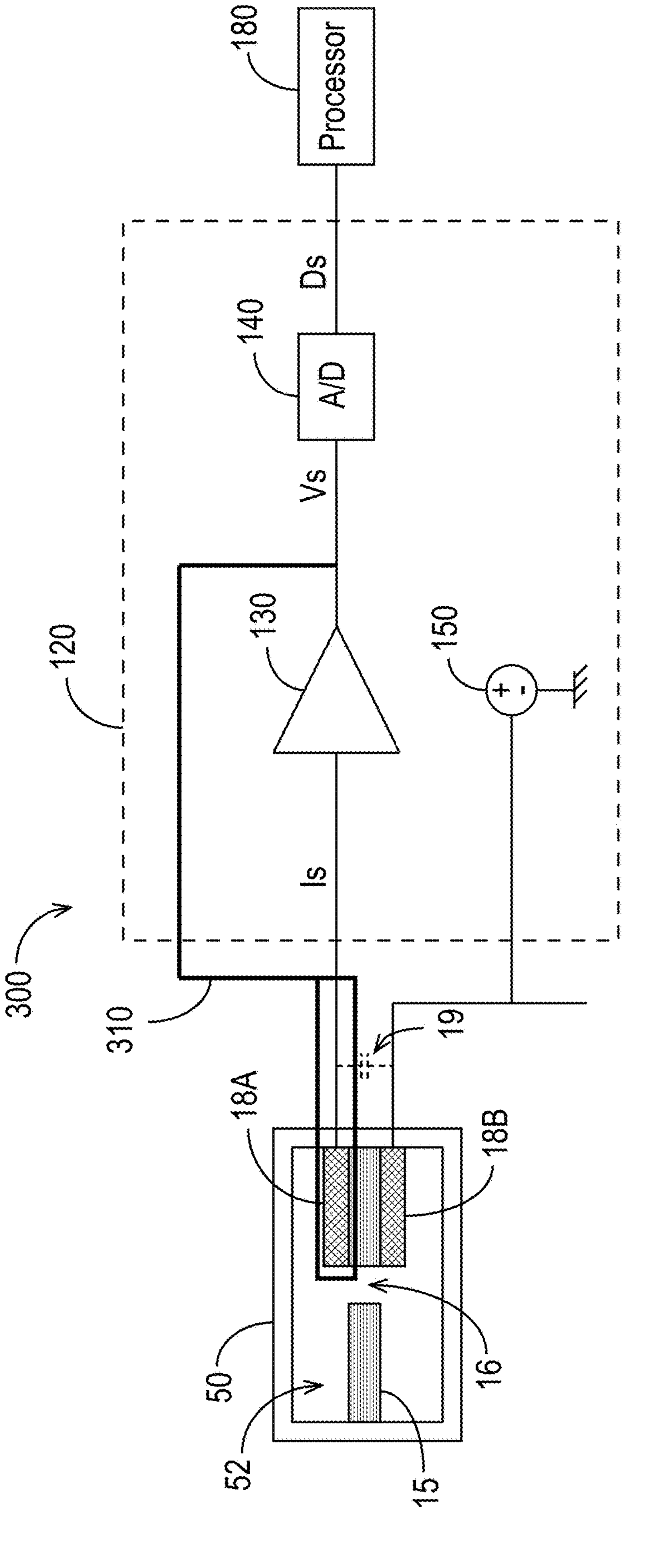
FIG. 5A is a diagram illustrating conceptually how a shield can be added to a system in accordance with some embodiments.

FIG. 5A is a diagram illustrating conceptually how a shield 310 can be added to a system 300 in accordance with some embodiments. As illustrated, the shield 310 can be coupled to the output of the amplifier 130, thereby substantially isolating the sense electrode 18A from the counter electrode 18B. The effect of the shield 310 is to reduce the parasitic capacitance 19 between the sense electrode 18A and the counter electrode 18B (illustrated by the parasitic capacitance 19 having a smaller size and being shown in dashed lines in FIG. 5A). The shield 310 can comprise any conductive material. Examples include, but are not limited to, Al, W, Pt, Cu, TiN, polysilicon, doped semiconductors, or a two-dimensional material such as graphene.

Figure 5B:
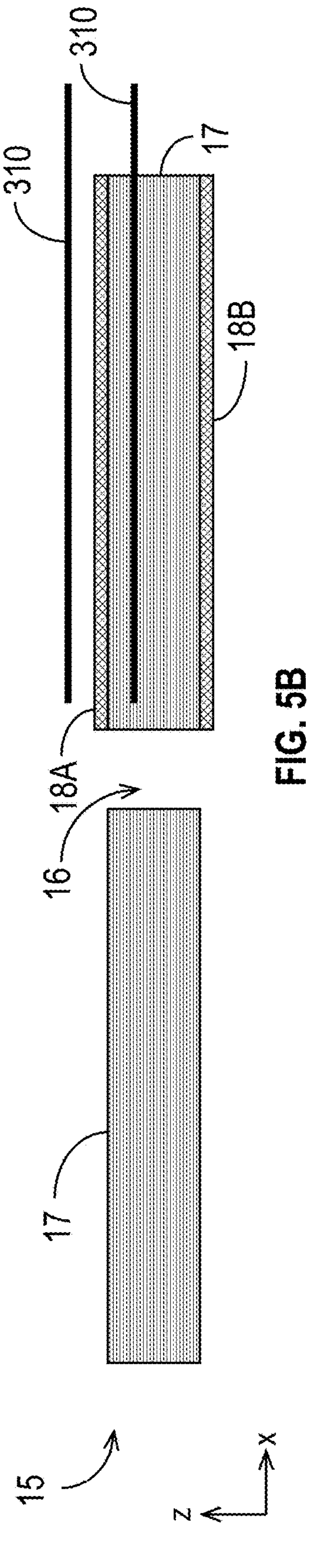
FIG. 5B illustrates a cross-section of an example configuration of a nanopore with a shield in accordance with some embodiments.

FIG. 5B illustrates a cross-section of an example configuration of a nanopore 15 with a shield 310 in accordance with some embodiments. The cross-section is in the x-z plane, as indicated by the axes. As illustrated in the example of FIG. 5B, a shield 310 fed from the output of the amplifier 130 can partially surround the sense electrode 18A to isolate it from the counter electrode 18B. In the example shown in FIG. 5B, the shield 310 is recessed from the hole 16. It will be appreciated that the current is measured between the sense electrode 18A and counter electrode 18B, and recessing the shield 310 may reduce or eliminate interference with the measurement. No particular recess distance is required. The recess distance should be selected so that the shield 310 does not interfere with the operation of the nanopore 15. For example, the recess distance may be 5-10 nm. It is to be understood that it may be possible for the recess distance to be negligible or even zero, depending on the implementation.

It is to be appreciated that the shield 310 is not connected to the sense electrode 18A in the example of FIG. 5B. The effect of the shield 310 is to mirror changes in the potential of the sense electrode 18A. If the potential of the shield 310 is held at the same potential as the sense electrode 18A, the parasitic capacitance 19 is canceled because there is no voltage across the parasitic capacitance 19. Accordingly, under this condition, the parasitic capacitance 19 will not divert any charge from the sense electrode 18A. In practice, it may not be possible to hold the shield 310 at the same potential as the sense electrode 18A, but practical implementations should be able to keep the potential close enough to substantially reduce the parasitic capacitance 19.

To maintain stability (e.g., reduce oscillations in the amplifier 130 output signal), a gain adjustment (e.g., to adjust the gain of the amplifier 130) can be provided. Too much feedback will lead to instability, but a large part of the parasitic capacitance can be canceled using a shield 310 as described herein.

In some embodiments, an integrated circuit is provided, and the nanopore 15 and the amplifier 130 (e.g., a CMOS amplifier) are integrated onto the same substrate. In some such embodiments, a source-follower transistor can be used as the amplifier 130, and the shield 310 can be connected to the source terminal of the transistor. As will be appreciated by those having ordinary skill in the art, the source-follower is a simple amplifier with a gain of around 1, and the source follows the gate. Alternatively, as will be appreciated by those having ordinary skill in the art, to increase the transconductance, the amplifier 130 can have a more sophisticated design (e.g., using multiple transistors). For example, FIG. 6 illustrates one example amplifier circuit 131 that comprises a field effect transistor, namely a MOSFET transistor 132, connected to an input voltage source 331.

Figure 6:
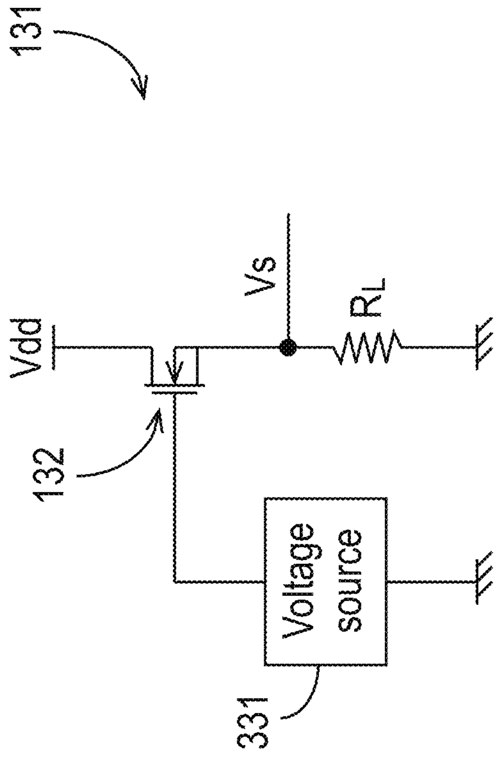
FIG. 6 illustrates an example amplifier circuit that comprises a MOSFET transistor connected to an input voltage source in accordance with some embodiments.
Figure 7A:
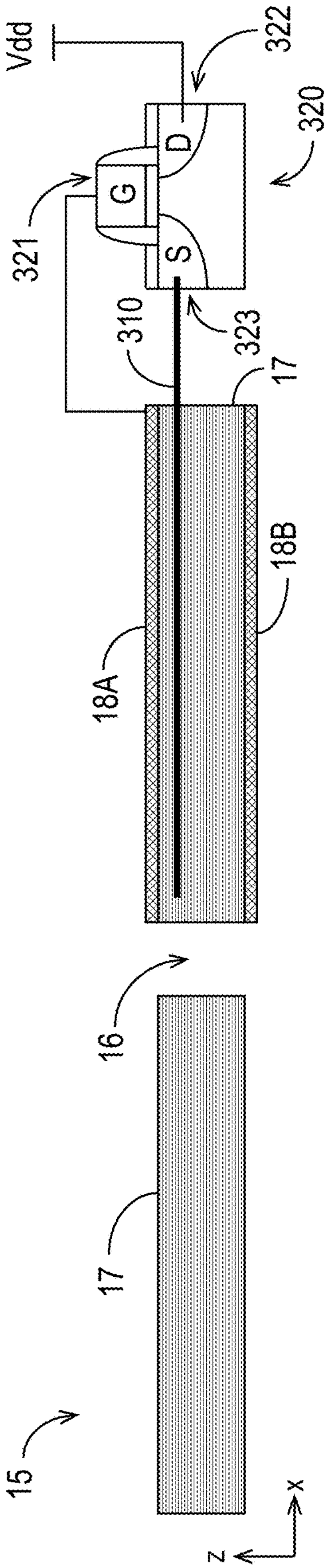
FIGS. 7A and 7B illustrate an example configuration that includes a transistor and a shield integrated with the nanopore in accordance with some embodiments.
Figure 7C:
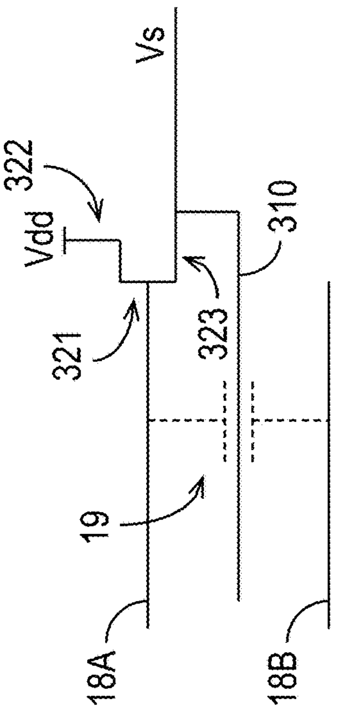
FIG. 7C shows conceptually that the use of the shield reduces the parasitic capacitance by isolating the sense electrode from the counter electrode in accordance with some embodiments.
Figure 7B:
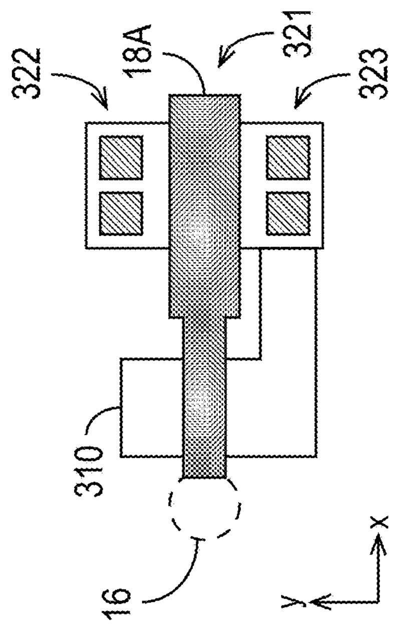

In an alternative configuration, a BiCMOS process can be used to create an amplifier 130 using a bipolar junction transistor (BJT), which has higher transconductance than the MOSFET transistor 132 shown in FIG. 6. FIGS. 7A, 7B, and 7C illustrate an example configuration that includes a transistor 320 and a shield 310 integrated with the nanopore 15 in accordance with some embodiments. FIG. 7A is a cross-section view of an example configuration in accordance with some embodiments. The cross-section is in the x-z plane, as indicated by the axes. As shown in FIG. 7A, the amplifier 130 comprises a transistor 320, which may be a BJT integrated onto the same substrate as the nanopore 15 to provide good transconductance. In the illustrated example, the gate 321 of the transistor 320 is coupled to the sense electrode 18A, the drain 322 is coupled to Vdd, and the source 323 is coupled to the shield 310. As will be appreciated by those having ordinary skill in the art, the transistor 320 mirrors the voltage on the sense electrode 18A on the source 323, which is connected to the shield 310. (It should be appreciated that FIG. 7A does not illustrate bias circuitry, such as resistors.)

FIG. 7B shows the configuration of FIG. 7A from above, in an x-y plane. As shown in the example configuration, the shield 310 passes under the sense electrode 18A (between the sense electrode 18A and the counter electrode 18B, which is not visible in the view of FIG. 7B). FIG. 7C shows conceptually that the use of the shield 310 "breaks," and thereby reduces, the parasitic capacitance 19 by isolating the sense electrode 18A from the counter electrode 18B. By holding the shield 310 at substantially the same voltage as the output voltage (Vs), the parasitic capacitance 19 will not divert a significant amount of charge from the sense electrode 18A.

It is to be appreciated that in a practical implementation, the shield 310 may not be able to completely surround the sense electrode 18A (e.g., it may not be able to perfectly isolate the sense electrode 18A from the counter electrode 18B) without causing a short circuit or other performance degradations. In some embodiments, the end of the shield 310 is close to the hole 16 but does not protrude to the edge of the hole 16 (e.g., as illustrated in FIGS. 7A and 7B). In other words, the shield 310 is recessed from the hole 16. As explained above, recessing the shield 310 may reduce or eliminate interference with the current measurement, but some embodiments might not recess the shield 310. Even with the constraint that the shield 310 does not extend to the hole 16, the use of a shield 310 can dramatically reduce the amount of charge that is diverted to the parasitic capacitance 19.

If additional cancellation of the parasitic capacitance 19 is desired, an implementation can use both a shield 310 and a feedback circuit, as described, for example, in U.S. patent application Ser. No. 17/651,254, filed Feb. 16, 2022, which is incorporated by reference in its entirety. Similarly, the bootstrapping approach described in U.S. patent application Ser. No. 17/651,254 can be used in conjunction with a shield 310.

Figure 8:
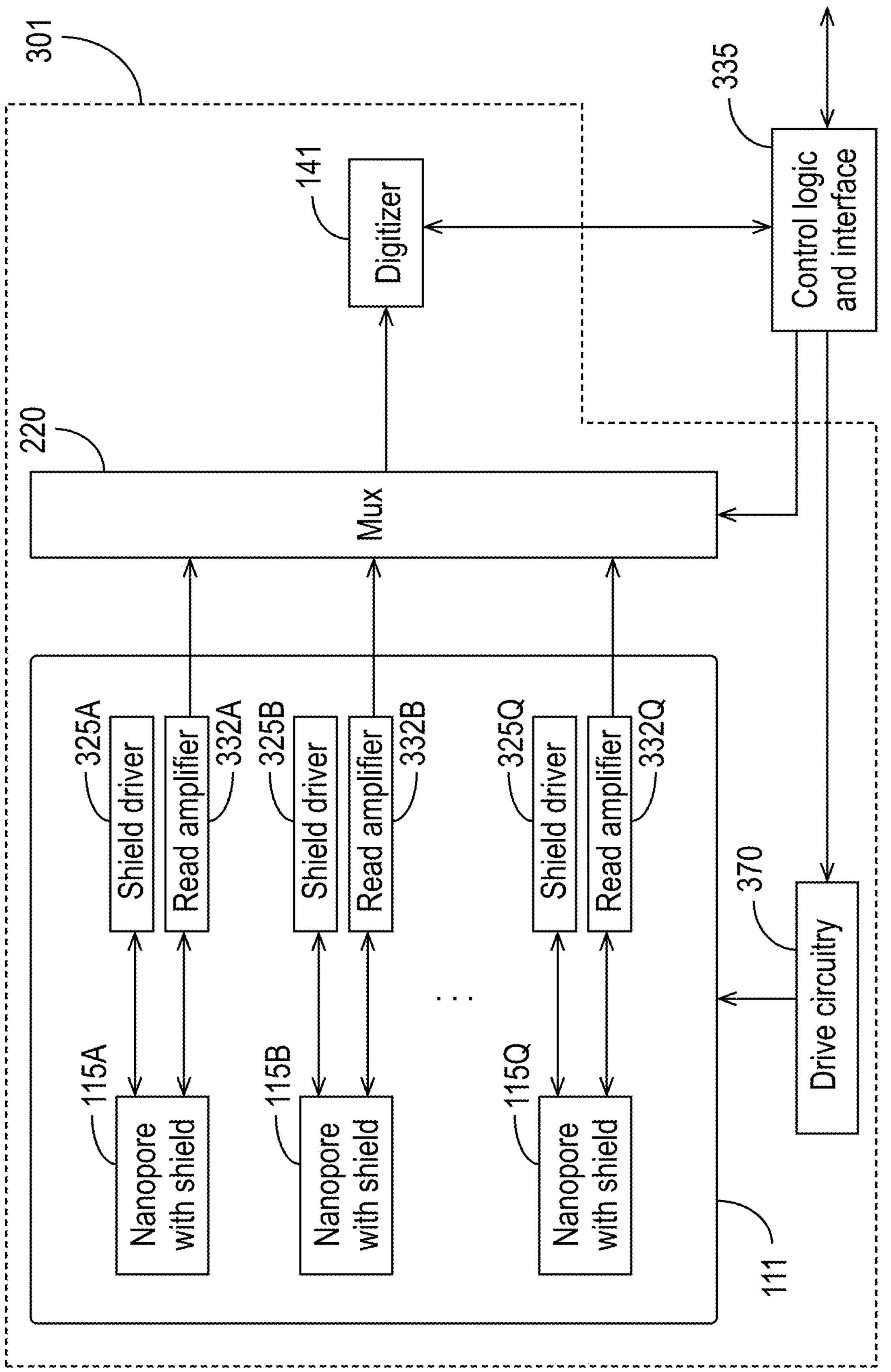
FIG. 8 is an illustration of an example system in accordance with some embodiments.

FIG. 8 is an illustration of an example system 301 in accordance with some embodiments. The system 301 includes an array 111 of nanopore units 115, each of which comprises a nanopore 15 with a respective shield 310, a sense electrode 18A, and a counter electrode 18B, as described above in, for example, the discussions of FIGS. 5A, 5B, 6, 7A, 7B, and 7C. The shield 310 of each nanopore unit 115 is coupled to a respective shield driver 325, and the sense electrode 18A of each nanopore unit 115 is coupled to a respective amplifier 332. In the example array 111 of FIG. 8, the nanopore unit 115A is coupled to the shield driver 325A and the read amplifier 332A; the nanopore unit 115B is coupled to the shield driver 325B and the read amplifier 332B; and the nanopore unit 115Q is coupled to the shield driver 325Q and the read amplifier 332Q. It is to be appreciated that the array 111 can include fewer or more combinations of components than shown. Moreover, the use of the letter "Q" in the last illustrated nanopore unit 115 is not intended to suggest that the array 111 of the system 301 includes any particular number of nanopore units 115 and associated shield drivers 325 and read amplifiers 332. In general, the array 111 can include any number of nanopore units 115 and associated components. The nanopore unit 115A, the nanopore unit 115B, the nanopore unit 115Q, and any other nanopore units 115 in the array 111 may be configured as illustrated and described above in the discussions of FIGS. 5A, 5B, 6, 7A, 7B, and/or 7C. Similarly, the read amplifiers 332A, 332B, 332Q, etc. may have the configurations and characteristics of the amplifiers 130 described above in the context of FIGS. 5A, 5B, 6, 7A, 7B, and/or 7C.

The read amplifiers 332 of the array 111 are coupled to a multiplexer. In the example of FIG. 8, the read amplifier 332A, read amplifier 332B, and read amplifier 332Q (and any other read amplifier(s) 332) of the array 111 are coupled to a multiplexer 220, which can operate to select individual nanopore units 115. Specifically, as shown in FIG. 8, the multiplexer 220 has a plurality of inputs, each corresponding to a respective one of the nanopore units 115 in the array 111, and a single output. The multiplexer 220 may be, for example, configured to cycle through individual nanopore units 115 of the array 111 to read each of the nanopores 15 in a systematic way (e.g., periodically, in accordance with a clock signal, in response to an instruction from the control logic and interface 335 discussed below, etc.). Alternatively or in addition, the multiplexer 220 may be configured to select any one of the nanopore units 115 in the array 110 at any time (e.g., when desirable or necessary) and to read its nanopore 15 (e.g., provide a signal representing its current to the amplifier 130). Accordingly, as illustrated in FIG. 8, in the system 301, a plurality (some or all) of the nanopore units 115 in the array 111 are coupled to the multiplexer 220.

The output of the multiplexer 220 is coupled to a digitizer 141, which may be, for example, an analog-to-digital converter 140 as described above.

In the example illustrated in FIG. 8, the system 301 is coupled to control logic and interface 335. In particular, the digitizer 141 and the drive circuitry 370 are coupled to the control logic and interface 335. The control logic and interface 335 may send to and/or receive signals and/or instructions from the drive circuitry 370 and/or the digitizer 141, and it may make the results of a measurements/reads of the nanopore units 115 available to a downstream system via any suitable interface (e.g., wired or wireless). The control logic and interface 335 may, for example, obtain a digitized signal from the digitizer 141 and make it available via interface.

The control logic and interface 335 is also coupled to and configured to provide signals/instructions to the multiplexer 220. For example, the control logic and interface 335 can provide a signal to cause the multiplexer 220 to cycle through the connected nanopore units 115 to allow the nanopore 15 currents to be read/measured. Alternatively or in addition, the control logic and interface 335 can select a particular nanopore unit 115 connected to the multiplexer 220 by providing a signal to the multiplexer 220.

The drive circuitry 370 is coupled to the array 111 and, as its name suggests, is the driver for the nanopore units 115 of the array 111. For example, the drive circuitry 370 may include the voltage source 150 illustrated in FIG. 2. The drive circuitry 370 is the power supply that biases the array 111, and it includes at least one drive circuit coupled to at least one of the nanopore units 115. In some embodiments, the drive circuitry 370 is configured to ensure that only one read amplifier 332 provides a signal to the multiplexer 220 at a time. It is to be appreciated that the control logic and interface 335 could, alternatively or in addition, control the selection by the multiplexer 220 of a particular read amplifier 332. FIG. 8 illustrates a single instance of drive circuitry 370 that can drive all of the nanopore units 115 in the array 111. It is to be understood that there may be multiple instances of drive circuitry 370, each of which drives a respective group of nanopore units 115.

Figure 9:
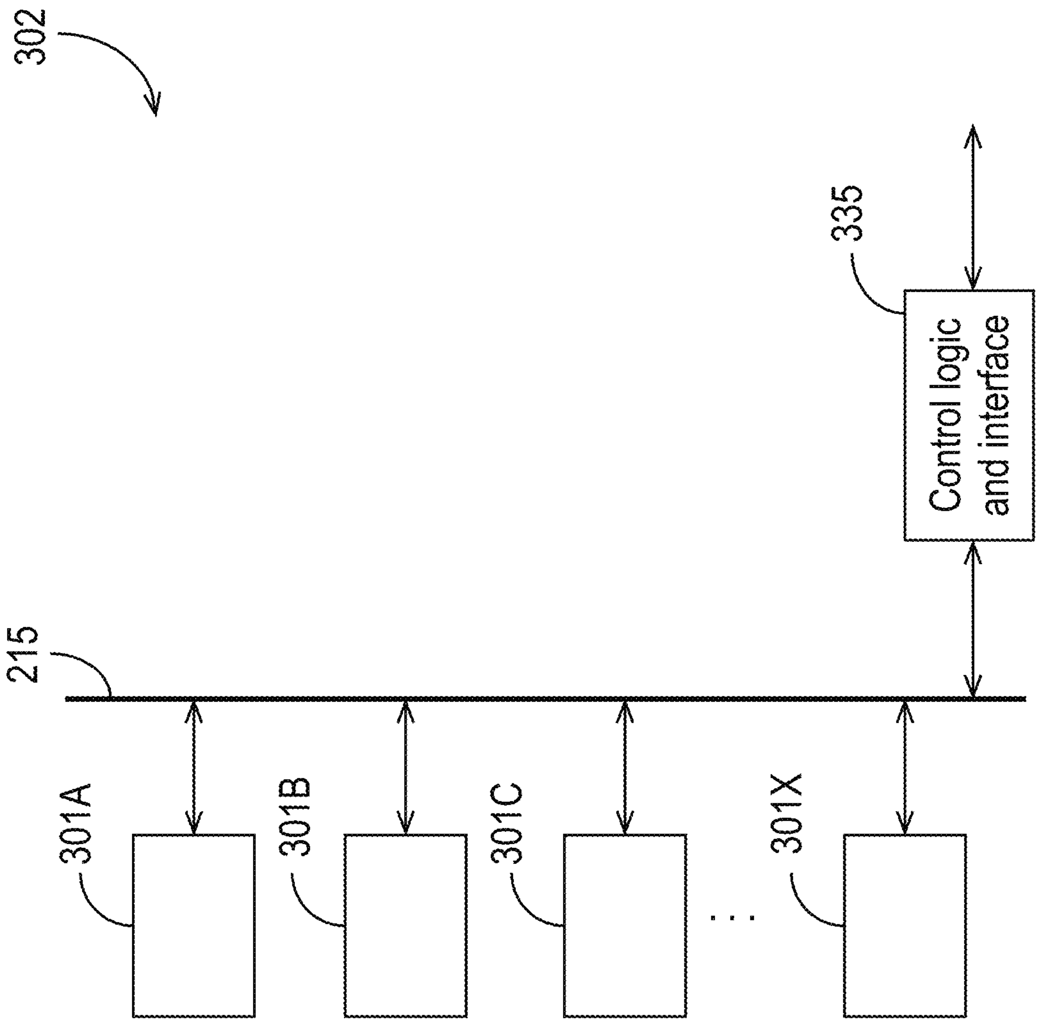
FIG. 9 illustrates another example of a system in accordance with some embodiments.

FIG. 9 illustrates another example of a system 302 in accordance with some embodiments. As illustrated, the system 302 includes one or more of the system 301 described above, thereby making them subsystems of the system 302. In the example shown in FIG. 9, the system 302 includes a plurality of systems 301 as subsystems. FIG. 9 illustrates and labels the subsystem 301A, the subsystem 301B, the subsystem 301C, and the subsystem 301X, but it is to be appreciated that the system 302 can include any number of systems 301 as subsystems. Moreover, the use of the letter "X" in the last illustrated system 301 is not intended to suggest that the system 302 includes any particular number of instances of systems 301 as subsystems.

The subsystem 301A, subsystem 301B, subsystem 301C, . . . , subsystem 301X (collectively, the subsystems 301*x*) of FIG. 9 are coupled to a bus 215. The bus 215 may be any suitable wired or wireless communication channel that allows the subsystems 301*x* in the system 302 to communicate with the control logic and interface 335. The control logic and interface 335 is configured to provide instructions/commands to and receive information/data from the subsystems 301*x*. The control logic and interface 335 includes an interface that may communicate, wirelessly and/or via a wired communication path, with downstream components (e.g., processor, memory) using any suitable protocol. For example, it may provide communication via Wi-Fi, Ethernet, USB, etc.

Figure 10:
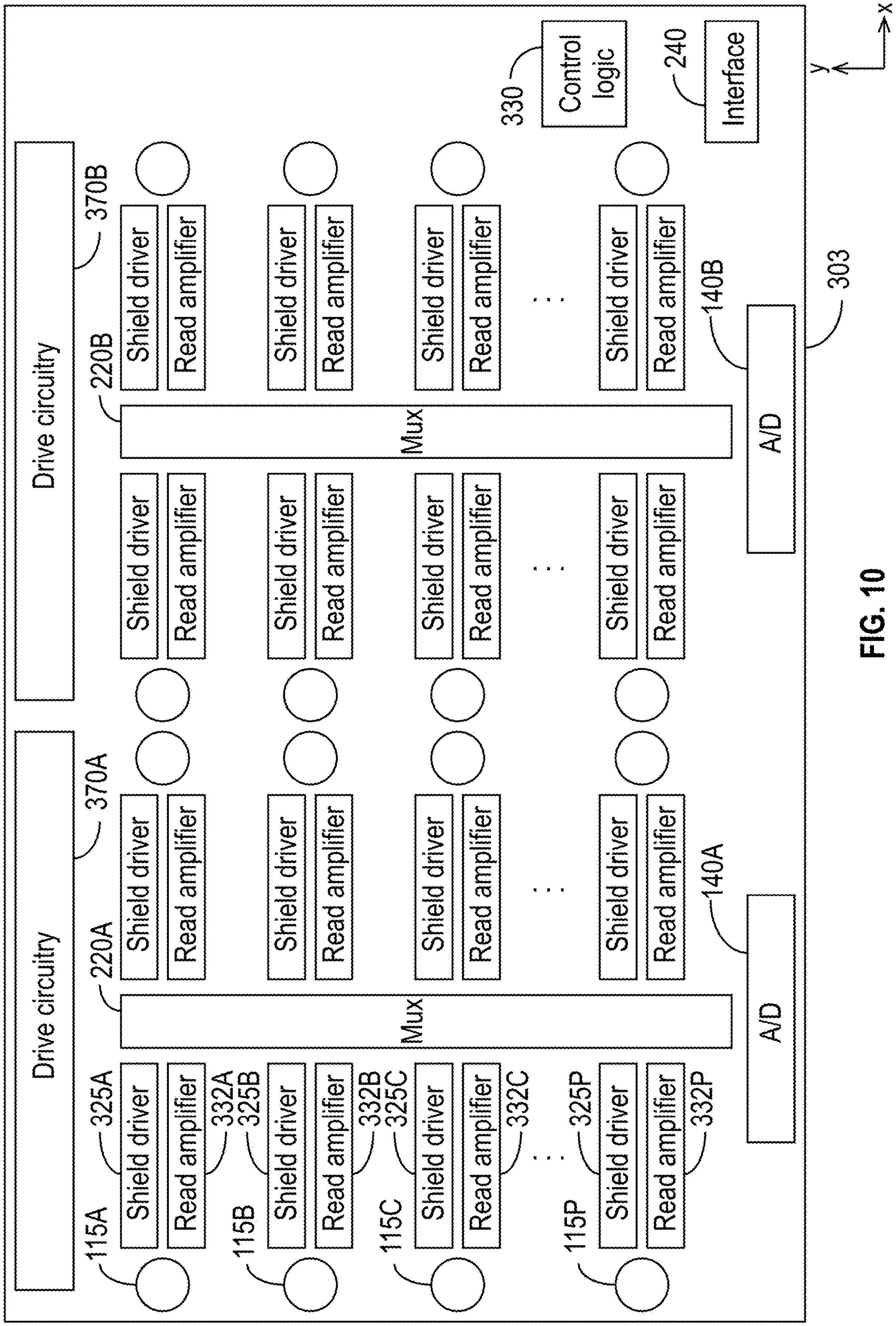
FIG. 10 illustrates an example of a device in accordance with some embodiments.

FIG. 10 illustrates an example of a device 303 in accordance with some embodiments. The device 303 may be, for example, an implementation of the system 302 shown in FIG. 9. The device 303 may be, for example, an integrated circuit chip that allows molecules to be detected. FIG. 10 is a diagram showing a plan view (e.g., in an x-y plane perpendicular to the x-z plane shown in FIG. 1 and others herein) of the device 303. As shown, the device 303 includes a plurality of nanopore units 115. To avoid obscuring the drawing, only four nanopore units 115 are labeled: nanopore unit 115A, nanopore unit 115B, nanopore unit 115C, and nanopore unit 115P. It is to be understood that the 303 can include any number of nanopore units 115.

As explained in the discussion of FIGS. 8 and 9, the nanopore units 115 are coupled to multiplexers 220. In FIG. 10, each nanopore unit 115 is coupled to a respective shield driver 325 and a respective read amplifier 332. Specifically, the nanopore unit 115A is coupled to the shield driver 325A and the read amplifier 332A, the nanopore unit 115B is coupled to the shield driver 325B and the read amplifier 332B, the nanopore unit 115C is coupled to the shield driver 325C and the read amplifier 332C, and the nanopore unit 115P is coupled to the shield driver 325P and the read amplifier 332P. As explained above, the read amplifiers 332 may be high-impedance buffer amplifiers.

Respective pluralities (subsets) of nanopore units 115, shield drivers 325, and read amplifiers 332 are coupled to the multiplexer 220A and multiplexer 220B. The analog-to-digital converter 140A is coupled to the multiplexer 220A, and the analog-to-digital converter 140B is coupled to the multiplexer 220B. The nanopore units 115 coupled to the multiplexer 220A are coupled to and driven by the drive circuitry 370A, and the nanopore units 115 coupled to the multiplexer 220B are coupled to and driven by the drive circuitry 370B. The device 303 also includes an interface 240 and control logic 330 (illustrated as the combined control logic and interface 335 block in FIGS. 8 and 9). The control logic 330 may, for example, obtain digitized signals representing current through a nanopore 15 from the analog-to-digital converter 140A and/or analog-to-digital converter 140B. The control logic 330 may make digitized signals available via the interface 240, as described above. The device 303 may also include memory (not illustrated).

FIG. 10 illustrates two multiplexers 220, two instances of the drive circuitry 370, and two analog-to-digital converters 140, but it is to be appreciated that the device 303 can include any number of these components. As explained above in the discussion of FIG. 9, any number of subsystems may be included in a system or device. Moreover, each set of multiplexer 220, drive circuitry 370, and analog-to-digital converter 140 may be coupled to any number of nanopore units 115. The examples shown herein are not intended to be limiting. The nanopore units 115 in FIG. 10 may be as described, for example, in the context of figures described above (e.g., FIGS. 5A-7C).

Figure 11:
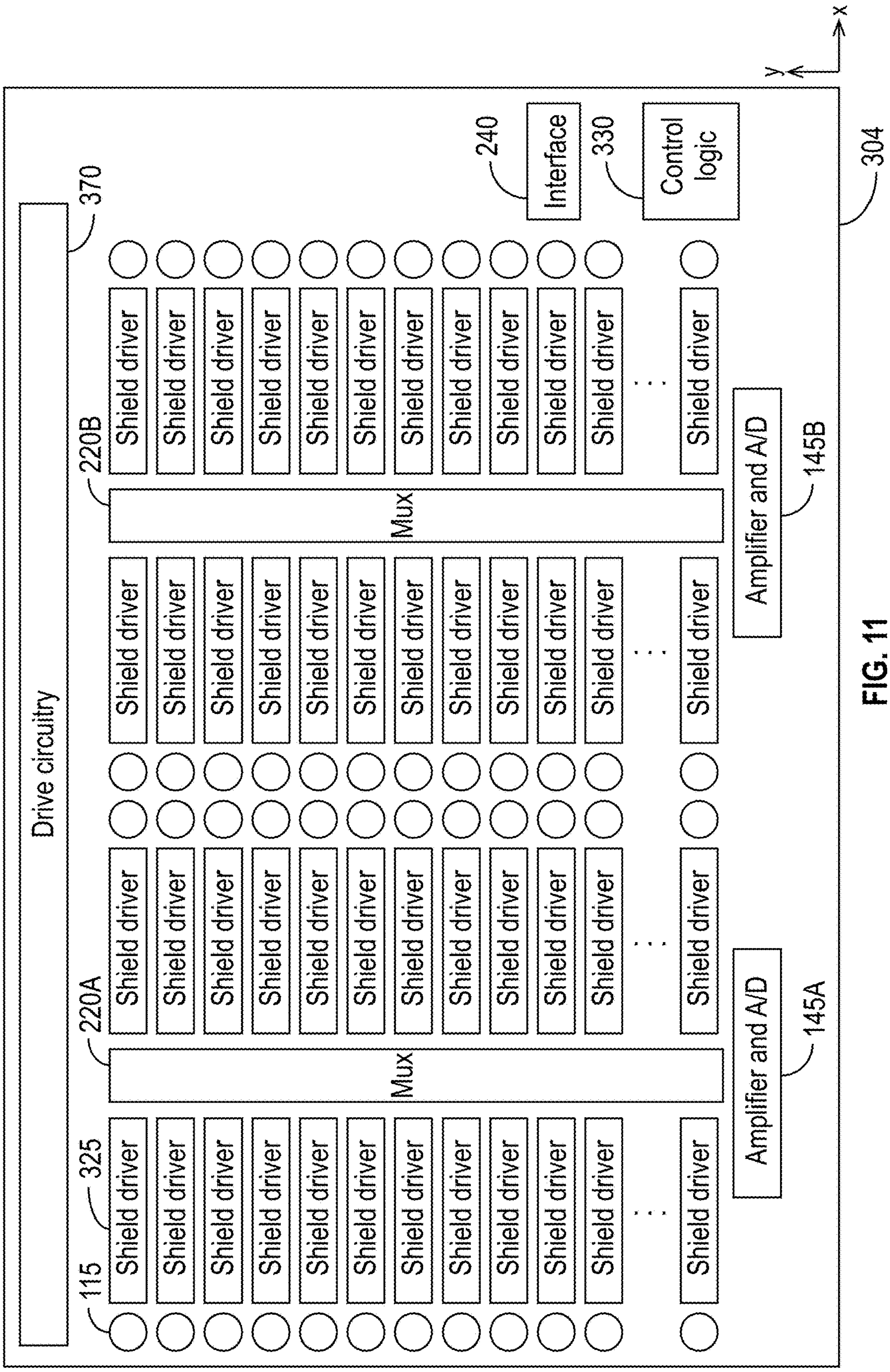
FIG. 11 illustrates an example of another device in accordance with some embodiments.

FIG. 11 illustrates an example of another device 304 in accordance with some embodiments. In the device 304, each of the nanopore units 115 includes a respective shield 310 that is coupled to a respective associated shield driver 325, but pluralities of nanopore units 115 and associated shield drivers 325 share an amplifier 130 and an analog-to-digital converter 140 (or, more generally, a digitizer), shown as a single block. As shown in the example of FIG. 11, a first plurality of nanopore units 115 and associated shield drivers 325 is coupled to the multiplexer 220A, which is coupled to the amplifier and analog-to-digital converter block 145A. The amplifier and analog-to-digital converter block 145A may be configured to perform the functions described above for the read amplifiers 332 and analog-to-digital converters 140. Similarly, a second plurality of nanopore units 115 and associated shield drivers 325 is coupled to the multiplexer 220B, which is coupled to the amplifier and analog-to-digital converter block 145B. (It is to be appreciated that the amplifier and analog-to-digital converter block 145A and the amplifier and analog-to-digital converter block 145B are shown as single blocks for convenience, and that an implementation may separate the read amplifier 332 from the analog-to-digital converter 140.) The device 304 also includes drive circuitry 370, which may be shared by all nanopore units 115. The device 304 also includes control logic 330 and an interface 240, which are illustrated as separate blocks in FIG. 11. The components and/or functionalities of the control logic 330 and interface 240 were described above in the discussion of FIG. 10 and in the discussion of the control logic and interface 335. Those descriptions apply to the control logic 330 and interface 240 here and are not repeated.

As illustrated by the example configurations shown in FIGS. 5A through 11, each nanopore 15 has a respective shield 310 that is configured to mitigate the effects of the parasitic capacitance 19 between the sense electrode 18A and the counter electrode 18B of the nanopore unit 50. As illustrated in FIGS. 8 through 11, certain other components (e.g., drive circuitry 370, control logic and interface 335, interface 240, control logic 330, analog-to-digital converter 140, amplifier and analog-to-digital converter blocks 145, amplifier 130, read amplifiers 332, etc.) can be shared by multiple nanopore units 115.

In the foregoing description and in the accompanying drawings, specific terminology has been set forth to provide a thorough understanding of the disclosed embodiments. In some instances, the terminology or drawings may imply specific details that are not required to practice the invention.

To avoid obscuring the present disclosure unnecessarily, well-known components are shown in block diagram form and/or are not discussed in detail or, in some cases, at all.

Unless otherwise specifically defined herein, all terms are to be given their broadest possible interpretation, including meanings implied from the specification and drawings and meanings understood by those skilled in the art and/or as defined in dictionaries, treatises, etc. As set forth explicitly herein, some terms may not comport with their ordinary or customary meanings.

As used in the specification and the appended claims, the singular forms “a,” “an” and “the” do not exclude plural referents unless otherwise specified. The word “or” is to be interpreted as inclusive unless otherwise specified. Thus, the phrase “A or B” is to be interpreted as meaning all of the following: "both A and B," "A but not B," and "B but not A." Any use of "and/or" herein does not mean that the word "or" alone connotes exclusivity.

As used in the specification and the appended claims, phrases of the form "at least one of A, B, and C," "at least one of A, B, or C," "one or more of A, B, or C," and "one or more of A, B, and C" are interchangeable, and each encompasses all of the following meanings: "A only," "B only," "C only," "A and B but not C," "A and C but not B," "B and C but not A," and "all of A, B, and C."

To the extent that the terms "include(s)," "having," "has," "with," and variants thereof are used in the detailed description or the claims, such terms are intended to be inclusive in a manner similar to the term "comprising," i.e., meaning "including but not limited to."

The terms "exemplary" and "embodiment" are used to express examples, not preferences or requirements.

The term "coupled" is used herein to express a direct connection/attachment as well as a connection/attachment through one or more intervening elements or structures.

The terms "over," "under," "between," and "on" are used herein refer to a relative position of one feature with respect to other features. For example, one feature disposed "over" or "under" another feature may be directly in contact with the other feature or may have intervening material. Moreover, one feature disposed "between" two features may be directly in contact with the two features or may have one or more intervening features or materials. In contrast, a first feature "on" a second feature is in contact with that second feature.

The term "substantially" is used to describe a structure, configuration, dimension, etc. that is largely or nearly as stated, but, due to manufacturing tolerances and the like, may in practice result in a situation in which the structure, configuration, dimension, etc. is not always or necessarily precisely as stated. For example, describing two lengths as "substantially equal" means that the two lengths are the same for all practical purposes, but they may not (and need not) be precisely equal at sufficiently small scales (e.g., if the units of a measurement are meters, two features having lengths of 1.000 m and 1.001 m would have substantially equal lengths). As another example, a structure that is "substantially vertical" would be considered to be vertical for all practical purposes, even if it is not precisely at 90 degrees relative to horizontal.

The drawings are not necessarily to scale, and the dimensions, shapes, and sizes of the features may differ substantially from how they are depicted in the drawings.

Although specific embodiments have been disclosed, it will be evident that various modifications and changes may be made thereto without departing from the broader spirit and scope of the disclosure. For example, features or aspects of any of the embodiments may be applied, at least where practicable, in combination with any other of the embodiments or in place of counterpart features or aspects thereof. Accordingly, the specification and drawings are to be regarded in an illustrative rather than a restrictive sense.

The invention claimed is:

1. A device for detecting molecules, the device comprising:

a multiplexer;

a read amplifier coupled to the multiplexer;

a digitizer coupled to the read amplifier;

a first nanopore;

a first sense electrode situated on a first side of the first nanopore;

a first counter electrode situated on a second side of the first nanopore;

a first shield, wherein the first shield at least partially surrounds the first sense electrode and is coupled to the multiplexer;

a first shield driver coupled to the first shield;

drive circuitry coupled to the first sense electrode; and control logic coupled to the drive circuitry, the multiplexer, and to the digitizer, wherein the control logic is configured to:

control at least one of the drive circuitry or the multiplexer to select at least one of the first sense electrode or the first counter electrode, and obtain a digitized signal from the digitizer, the digitized signal representing a current through the first nanopore.

2. The device recited in claim 1, further comprising an interface coupled to the control logic, and wherein the control logic is further configured to make the digitized signal available via the interface.

3. The device recited in claim 1, wherein:

the first nanopore comprises a first hole, and wherein the first shield is recessed from the first hole.

4. The device recited in claim 1, wherein the drive circuitry comprises a voltage source.

5. The device recited in claim 1, wherein the digitized signal is a first digitized signal, and further comprising:

a second nanopore;

a second sense electrode situated on a first side of the second nanopore;

a second counter electrode situated on a second side of the second nanopore;

a second shield, wherein the second shield at least partially surrounds the second sense electrode and is coupled to the multiplexer; and a second shield driver coupled to the second shield, and wherein control logic is further configured to:

control the at least one of the drive circuitry or the multiplexer to select at least one of the second sense electrode or the second counter electrode, and obtain a second digitized signal from the digitizer, the second digitized signal representing a current through the second nanopore.

6. The device recited in claim 1, wherein the multiplexer is a first multiplexer, the read amplifier is a first read amplifier, and the digitizer is a first digitizer, and further comprising:

a second multiplexer;

a third nanopore;

a third sense electrode situated on a first side of the third nanopore;

a third counter electrode situated on a second side of the third nanopore;

a third shield, wherein the third shield at least partially surrounds the third sense electrode and is coupled to the second multiplexer;

a third shield driver coupled to the third shield;

a second read amplifier coupled to the second multiplexer; and a second digitizer coupled to the second read amplifier, and wherein:

the drive circuitry is further coupled to the third sense electrode, the control logic is further coupled to the second multiplexer and to the second digitizer, and the control logic is further configured to:

control at least one of the drive circuitry or the second multiplexer to select at least one of the third sense electrode or the third counter electrode, and obtain a second digitized signal from the second digitizer, the second digitized signal representing a current through the third nanopore.

7. A system for detecting molecules, the system comprising:

an array comprising:

a first read amplifier;

a first nanopore;

a first sense electrode situated on a first side of the first nanopore;

a first counter electrode situated on a second side of the first nanopore;

a first shield, wherein the first shield at least partially surrounds the first sense electrode and is coupled to an output of the first read amplifier;

a first shield driver coupled to the first shield;

a second read amplifier;

a second nanopore;

a second sense electrode situated on a first side of the second nanopore;

a second counter electrode situated on a second side of the second nanopore; and a second shield, wherein the second shield at least partially surrounds the second sense electrode and is coupled to an output of the second read amplifier; and a second shield driver coupled to the second shield;

drive circuitry coupled to the array;

a multiplexer, wherein a first input of the multiplexer is coupled to the first read amplifier and a second input of the multiplexer is coupled to the second read amplifier, and an output of the multiplexer is coupled to a digitizer; and control logic coupled to the drive circuitry, to the digitizer, and to the multiplexer, wherein the control logic is configured to:

control at least one of the drive circuitry or the multiplexer to select at least one of the first sense electrode or the first counter electrode, and obtain a digitized signal from the digitizer, the digitized signal representing a current through the first nanopore.

8. The system recited in claim 7, further comprising an interface coupled to the control logic, and wherein the control logic is further configured to make the digitized signal available via the interface.

9. The system recited in claim 7, wherein:

the first read amplifier comprises a first transistor, and wherein the first shield is coupled to a source of the first transistor, and the first sense electrode is coupled to a gate of the first transistor; and the second read amplifier comprises a second transistor, and wherein the second shield is coupled to a source of the second transistor, and the second sense electrode is coupled to a gate of the second transistor.

10. The system recited in claim 9, wherein at least one of the first transistor or the second transistor is a field effect transistor or a bipolar junction transistor.

11. The system recited in claim 7, wherein:

the first nanopore comprises a first hole, and wherein the first shield is recessed from the first hole, and the second nanopore comprises a second hole, and wherein the second shield is recessed from the second hole.

12. The system recited in claim 7, wherein the digitized signal is a first digitized signal, and wherein control logic is further configured to:

control the at least one of the drive circuitry or the multiplexer to select at least one of the second sense electrode or the second counter electrode, and obtain a second digitized signal from the digitizer, the second digitized signal representing a current through the second nanopore.

13. The system recited in claim 7, wherein the drive circuitry comprises a voltage source.

14. A system for detecting molecules, the system comprising:

an amplifier;

a nanopore, wherein the nanopore is one of a plurality of nanopores in an array of nanopores;

a sense electrode situated on a first side of the nanopore;

a counter electrode situated on a second side of the nanopore;

a shield situated between the sense electrode and the counter electrode;

a digitizer coupled to an output of the amplifier; and control logic coupled to the digitizer, wherein:

the sense electrode and the counter electrode are configured to sense a current through the nanopore, the control logic is configured to (a) select at least one of the sense electrode or the counter electrode using a multiplexer, and (b) obtain a digitized signal from the digitizer, the digitized signal representing the current through the nanopore sensed by the sense electrode and the counter electrode, and the shield at least partially surrounds the sense electrode and is coupled to an output of the amplifier.

15. The system recited in claim 14, further comprising a processor coupled to an output of the digitizer.

16. The system recited in claim 14, wherein the nanopore comprises a hole, and wherein the shield is recessed from the hole.

17. The system recited in claim 14, wherein the amplifier comprises a transistor, and wherein the shield is coupled to a source of the transistor, and the sense electrode is coupled to a gate of the transistor.

18. The system recited in claim 17, wherein the transistor and the nanopore are integrated onto a same substrate.

19. The system recited in claim 18, wherein the nanopore comprises a hole, and wherein the shield is recessed from the hole.

* * * * *